US006991806B1

(12) United States Patent
Dickinson et al.

(10) Patent No.: US 6,991,806 B1
(45) Date of Patent: Jan. 31, 2006

(54) PHARMACEUTICAL COMPOSITIONS COMPRISING IBUPROFEN AND DOMPERIDONE

(75) Inventors: Jeffrey Dickinson, Nottingham (GB); Jayantilal Vithal Makwana, Nottingham (GB)

(73) Assignee: The Boots Company PLC, Nottingham (GB)

( * ) Notice: Subject to any disclaimer, the term of this patent is extended or adjusted under 35 U.S.C. 154(b) by 0 days.

(21) Appl. No.: 09/774,171

(22) PCT Filed: Aug. 4, 1999

(86) PCT No.: PCT/EP99/05753

§ 371 (c)(1),
(2), (4) Date: Feb. 1, 2001

(87) PCT Pub. No.: WO00/07570

PCT Pub. Date: Feb. 17, 2000

(30) Foreign Application Priority Data

Aug. 5, 1998 (GB) .................................... 9816899

(51) Int. Cl.
  *A61K 9/16* (2006.01)
  *A61K 9/50* (2006.01)
  *A61K 31/192* (2006.01)
(52) U.S. Cl. .................. 424/464; 424/465; 514/225.2; 514/568; 514/557
(58) Field of Classification Search ................ 424/465, 424/464, 489, 468, 469, 470, 466, 436, 441, 424/435, 456, 451; 514/225.2, 568, 577
See application file for complete search history.

(56) References Cited

U.S. PATENT DOCUMENTS

| | | |
|---|---|---|
| 3,160,562 A | 12/1964 | Cerletti et al. |
| 4,983,621 A | 1/1991 | Bunce et al. |
| 4,985,459 A | 1/1991 | Sunshine et al. |
| 5,053,429 A | 10/1991 | Hirsch et al. |
| 5,215,758 A | 6/1993 | Krishnamurthy |
| 5,273,759 A | 12/1993 | Simmons |
| 5,460,828 A | 10/1995 | Santus et al. |
| 5,587,179 A | 12/1996 | Gergely et al. |
| 5,814,339 A | 9/1998 | Prudhoe |
| 5,891,885 A | 4/1999 | Caruso |
| 5,985,874 A | 11/1999 | Owen et al. |
| 6,319,514 B1 * | 11/2001 | On .............................. 424/436 |

FOREIGN PATENT DOCUMENTS

| | | |
|---|---|---|
| CA | 2020 018 | 12/1991 |
| EP | 0 327 040 | 8/1989 |
| GB | 2 313 309 | 11/1997 |
| WO | 95/22974 | 8/1995 |
| WO | 98/34612 | 8/1998 |
| WO | 00/21534 | 4/2000 |

OTHER PUBLICATIONS

Postgraduate Medical Journal; "Headache", Ruth Atkinson, M.D. and Otto Appenzeller, M.D., Ph.D., 60:841-846, (Dec. 1984).
J. Clin Pharmacol, Therapeutic Review, "Current Concepts of Migraine Therapy", Seymour Diamond, M.D. and Ellen Millstein, M.D., 28:193-199, (1988).
The Medical Letter, On Drugs and Therapeutics; "Drugs for Migraine", vol. 26, Issue 673, pp. 95-96 (Oct. 26, 1984).
Br Med. J, "Treating Migraine", C. Clough, vol. 299, pp. 141-142 (Jul. 15, 1989).
Practical Therapeutics, "Migraine, Current Concepts of Pathogenesis and Treatment", Richard Peatfield, Drugs 26: 364-371, (1983).
Br. Med. J, "Sumatriptan in Migraine", JMS Pearce, vol. 303 (Dec. 14, 1991).
The Annals of Pharmacotherapy, "Sumatriptan: A Selective 5-Hydroxytryptamine Receptor Agonist For The Acute Treatment of Migraine", Terence Fullerton and Fran M. Gengo, vol. 26, pp. 800-808, (1992).
Eur N urol, "A Study to Compare Oral Sumatriptan with Oral Aspirin plus Oral Metoclopramide in the Acute Treatment of Migraine", Ms. C.J. Thomson, Study Coordinator, 32:177-184 (1992).
Cephalalgia, "Domperidone Plus Paracetamol in the Treatment of Migraine", E. Anne MacGregor, et al., 13(2):124-127 (1993).
Therapia. Hungarica, "The Role of a Peripheral Dopamine-Antagonist (Motilium) in Improving the Tolerance to Steroidal and Non-Steroidal Anti-Inflammatory Agents", Z. Zahumenszky, et al., vol. 38, pp. 156-159 (1990).
Postgrad. Med. J. Suppl., "The Effect of Domperidone on the Gastric Tolerance and Efficacy of Non-Steroidal Anti-Inflammatory Drugs on Osteo-Arthritis", L. Depuydt et al., vol. 55, No. 1, p. 52 (1979).
The Pharmaceutical Journal, "Migraine-Separate Administration of Antiemetic and Analgesic Drugs Recommended", p. 654, (Nov. 26, 1983).
Deutsche Apotheker Zeltung, "Selbstmedikation bei Migraene and Kopfschmerz vom Spannugstyp", H. Goebelvol. et al., 135, No. 9, (Mar. 2, 1995).
Nuova Rivista di Neurologia, "Linee-guida per II Trattamento Dell'attacco Acuto", Franco Granella, Suppl. al vol. 5, No. 6 (Dec. 1995).

(Continued)

Primary Examiner—Michael Hartley
(74) Attorney, Agent, or Firm—Rothwell, Figg, Ernst & Manbeck P.C.

(57) ABSTRACT

A stable pharmaceutical composition comprising a mixture of (i) an ibuprofen medicament; (ii) a domperidone medicament and (iii) a carrier material characterized in that the carrier material is substantially free of providone and comprises at least one diluent combined with at least one release modifying agent.

15 Claims, No Drawings

OTHER PUBLICATIONS

Meunch. Med. Wahr, *"Therapie des Medikamenteninduzierten Dauerkopfschmerzes"*, H.C. Diener et al., vol. 134, No. 10, pp. 159-162 (1992).

Abstract of Schmerz, *"Medical Therapy for Menstrual Migraine"*, V. Pfaffenrath et al., vol. 10, No. 3, pp. 146-148 (1996).

Adstract of Acta. Clin., *"Pharmacology of Migraine"*, V. Demarin et al., vol. 32, No. 2, pp. 81-89 (1995).

Abstract of Internist, *"Pain Therapy in Chronic Headache and Migraine"*, H.C. Diener, vol. 35, No. 1, pp. 26-31 (1994).

Abstract of Pain, *"Behavioural and Prophylactic Pharmacological Intervention Studies of Pediatric Migraine: An Exploatory Meta-analysis"*, C. Hermann et al., vol. 60, No. 3, pp. 329-356 (1995).

Abstract of Cephalagia, *"Analgesics and NSAIDs in the Treatment of the Acute Migraine Attack"*, V. Pfaffenrath et al., Suppl. 15, vol. 15, pp. 14-20 (1995).

Abstract of Eur-Neurol., *"A Review of Current Treatments for Migraine"*, H.C. Diener, Suppl. 2, vol. 34, pp. 18-25 (1994).

Abstract of Scott Med J., *"Migraine—Treatment of Acute Attack"*, V. Pfaffenrath et al., vol. 138, No. 23-24, pp 591-599 (1988).

Abstract of Scott Med J., "Migraine—Treatment of Acute Attack", M. Wilkinson, vol. 30, No. 4, pp 258-262 (1985).

Abstract of Cephalagia, "Treatment of the Acute Migraine Attack—Current Status", vol. 3, No. 1, pp 61-67 (1983).

Oesterr inhische Aetrzezeitung, "Migraene-Therapie", D. Klingler et al., vol. 49, No. 24, pp. 26-30 (1994).

Antimigraine Drugs, Tim Steiner, PhD, LLM, MB, BS, MFPM, *When and How To Use Antimigraine Drugs*, pp. 45-58, Prescriber, Apr. 5, 1995.

Goodman & Gilman's The Pharmacological of Basis of Therapeutics, Paul A. Insel, *Analgesic-Antipyretic and Antiinflammatory Agents and Drugs Employed in the Treatment of Gout*, (1996).

* cited by examiner

PHARMACEUTICAL COMPOSITIONS COMPRISING IBUPROFEN AND DOMPERIDONE

This application is the National Stage Application of PCT/EP99/05753 filed Aug. 4, 1999.

This invention relates to pharmaceutical compositions comprising an ibuprofen medicament and a domperidone medicament.

Ibuprofen, namely 2-(4-isobutylphenyl)propionic acid, is a well known medicament with analgesic, anti-inflammatory and anti-pyretic properties. It is usually sold in the form of racemic ibuprofen (equal amounts of the S(+)-ibuprofen and R(−)-ibuprofen enantiomers). It may also be in the form of the purified form of either enantiomer, especially S(+)-ibuprofen which is acknowledged to be the active form of racemic ibuprofen. Ibuprofen is also available in salt form, for example the sodium or lysine salt of ibuprofen. Ibuprofen is available under prescription (eg Brufen (RTM)), primarily for the treatment of painful and anti-inflammatory disorders including rheumatoid arthritis, ankylosing spondylitis, osteoarthritis, postoperative pain, post partum pain and soft tissue injuries, generally at doses up to 3200 mg per day. Ibuprofen is also available as a non-prescription drug (eg Nurofen (RTM)), primarily for the treatment of symptoms of pain and fever including headache, migraine, rheumatic pain, muscular pain, backache, neuralgia, dysmenorrhoea, dental pain and colds and flu, generally at doses up to 1200 mg per day. The commercially available ibuprofen tablets usually contain ibuprofen or an enantiomer or salt thereof equivalent to 200 mg, 400 mg, 600 mg or 800 mg racemic ibuprofen. Hereinafter the term "ibuprofen"means any enantiomer of ibuprofen or mixtures of enantiomers including the racemic mixture.

Domperidone, namely 5-chloro-1-[1-[3-(2,3-dihydro-2-oxo-1H-benzimidazol-1-yl)propyl-4-piperidinyl]-1,3-dihydro-2H-benzimidazol-2-one is a well known medicament with antiemetic properties. Domperidone is available under prescription [eg Motilium (RTM)] as tablets for the treatment of functional dyspepsia at doses of up to 80 mg per day and is also available as tablets, suspensions or suppositories for the treatment of emesis (in nausea or vomiting) at doses of up to 120 mg per day. Pharmaceutically acceptable salts, eg the maleate salt of domperidone may be used instead of domperidone itself. In this case the amount of active material is adjusted so as to administer an equivalent amount of domperidone base.

Administration of analgesic NSAIDs (such as ibuprofen) together with domperidone has been proposed for use in the treatment of migraine, see for example GB 2313309 and CA 2020018. When two actives are administered as a combined treatment, it is advantageous to provide them together in the same dosage form rather than administer them sequentially in different dosage forms. A generalised discussion of typical formulation excipients useful to provide unit dosage forms is provided in the references noted above but no compositions of ibuprofen and domperidone are specifically illustrated in these patent applications.

A problem has arisen however, that when it is desired to administer the ibuprofen and domperidone active ingredients in the same pharmaceutical formulation, it has been found that solid formulations may not be stable on storage.

In formulating solid dosage forms of active ingredients, a wide variety of excipients may be employed. These may be selected to provide a formulation that is sufficiently robust that it can withstand production, transportation and storage procedures. However, it is also important to ensure that the composition releases the active ingredients at an appropriate rate in the body following administration to the patient to allow each active ingredient to be provided in a precisely determined amount and to have the desired release profile to suit the therapeutic treatment for which it is administered. Thus, ingredients must be chosen which meet both requirements. Excipients which have cohesive properties to bind the combination of ingredients are important in formulating solid compositions. Further useful excipients are release modifying agents, such as disintegrating agents for conventional immediate release tablets and sustained release carriers where it is desired to release the medicaments over a longer period. When the dosage form is exposed to the aqueous medium after ingestion, these release modifying excipients cause the solid composition to release the active ingredient at a desired rate, for example substantially immediately or at a desired controlled rate. There may also be provided carrier materials which allow the homogeneous mixing of the active ingredients throughout the dosage form and which may aid compressibility of the tablets. Such carrier materials may have disintegrating properties and/or cohesive properties when used in certain proportions in the dosage form. Other excipients may also be added as necessary for particular drugs to provide appropriate release and absorption into the body.

In the production of solid dosage forms there is often a granulation stage in which the active ingredient is combined with an inert excipient and formed into a free-flowing, homogeneous granular composition which is capable of being mixed with other ingredients and formed into a solid dosage form. In this granulation stage, most commonly the powdered ingredients are mixed and then granulated with a granulating fluid (eg water or a pharmaceutically acceptable organic solvent such as an alcoholic solvent) to form a granular composition. A granulating agent which may be a solid and which further imparts cohesive properties to the granule may be present, either dissolved in the granulating liquid or mixed in with the powdered ingredients. Povidone is a preferred granulating agent as it is readily soluble both in water and in alcoholic solvents and it provides good cohesive properties to the resulting granule. Povidone has been used previously in providing both granular compositions of ibuprofen and granular compositions of domperidone. Povidone is of particular value in the manufacturing process because it allows changes in the composition of the granulating fluid (eg water may replace the alcoholic solvent or the water and alcohol may be combined in a desired proportion) without affecting the solid ingredients in the composition. Such changes in the granulating fluid may be necessary to optimise the quality of the granular product to ensure a desired solid composition is produced during the production scaling up process between lab scale and a full production batch. It is also of advantage to use povidone in the composition because its ready solubility contributes to the disintegration of the solid dosage form when in the gastrointestinal tract. Thus, povidone is acknowledged to be a preferred material, especially as granulating agent in compositions containing ibuprofen and is very widely used.

However, it has been found that compositions containing ibuprofen, domperidone and povidone are unstable on storage, for example leading to a reduction in the amount of active ingredient available for absorption, particularly domperidone.

This is a very significant finding for the above combination of active ingredients because povidone is such a widely used pharmaceutical excipient, particularly in the production of tablets. As well as affecting compositions containing granulated ibuprofen together with domperidone, the presence of povidone will also affect other solid formulations containing this combination of active ingredients and also any other composition wherein the ibuprofen, domperidone and povidone are combined, for example liquids and semi-solids.

Thus, in accordance with the invention we have now found a carrier system which provides stabilised formulations of ibuprofen and domperidone.

According to the invention there is provided a stable pharmaceutical composition comprising a mixture of: —
(i) an ibuprofen medicament;
(ii) a domperidone medicament; and
(iii) a carrier material characterised in that the carrier material is substantially free of povidone and comprises at least one diluent combined with at least one release modifying agent.

WO 98/34612 was published 13 Aug. 1998. The disclosure relates a combined drug treatment of an ibuprofen medicament with a domperidone medicament. Pharmaceutical compositions containing the two active ingredients suitable for administration to patients are discussed therein, including solid compositions for oral administration, liquid fill compositions and oral liquid compositions, compositions for topical administration, rectal administration and parenteral administration and also spray formulations. Some solid compositions are disclosed which may comprise a diluent, a lubricating agent, a disintegrating agent and optionally a binder and/or a flow aid. The preferred binder (which reflects the state of the art as given above) is said to be polyvinylpyrrolidone and this is reflected by its use as an excipient in a number of illustrative solid compositions. However, in the range of illustrative Examples provided, a number omit to use polyvinylpyrrolidone (see Examples 6 and 7 which granulate the ibuprofen and domperidone active ingredient with a carrier material consisting essentially of maize starch (at 35–38% of total tablet weight) and dried maize starch (at 3–4% of total tablet weight); Examples 8 and 9 disclose hard gelatin capsule compositions comprising a carrier consisting essentially of maize starch (at 15–20% by weight of total capsule contents) and pre-gelled starch (at 5–6% by weight of total capsule contents); Examples 9 and 10 also disclose tablets comprising granulated ibuprofen with a carrier consisting essentially of microcrystalline cellulose (at 10–11% total tablet weight) in combination with croscarmellose sodium (at 14–16% total tablet weight) and pre-gelled starch (at 10% of total tablet weight); Examples 15 and 16 directly compress all the ingredients, without a granulation stage, and comprise a carrier material consisting essentially of microcrystalline cellulose (at 8–11% total tablet weight) and lactose (at 5–6% of the total tablet weight).

However, there is no suggestion in WO 98/34612 of the advantages in stability to be obtained in a single dosage form comprising an ibuprofen medicament and a domperidone medicament by providing a carrier substantially free of polyvinylpyrrolidone. The compositions specifically disclosed in the above identified Examples of WO 98/34612 may be excluded from the scope of the present patent application where they constitute prior art. Such excluded subject matter can be considered to be:—
(a) a compressed tablet comprising granulated ibuprofen and a carrier material consisting essentially of either maize starch at 35–38% total tablet weight in combination with dried maize starch at 34% total tablet weight or microcrystalline cellulose at 10–11% total tablet weight in combination with croscarmellose sodium at 14–16% total tablet weight and pre-gelled starch at 10% total tablet weight;
(b) a direct compression tablet comprising a carrier material consisting essentially of microcrystalline cellulose at 8–11% total tablet weight and lactose at 5–6% total tablet weight;
(c) a hard gelatin capsule comprising a carrier consisting essentially of maize starch at 15–20% total capsule contents weight in combination with pre-gelled starch at 5–6% total capsule contents weight.

Povidone is the internationally accepted terminology for 1-Ethenyl-2-pyrrolidone homopolymer, also known as polyvinylpyrrolidone. Herein, the words 'povidone' and 'polyvinylpyrrolidone' are used interchangeably. Povidone is soluble in water. The term 'povidone' as used herein also includes 'crospovidone' which is a cross-linked homopolymer of N-vinyl-2-pyrrolidinone. The chemical name of crospovidone is 1-Ethenyl-2-pyrrolidinone homopolymer. Crospovidone is insoluble in water. It has been found that compositions comprising crospovidone are more unstable than compositions comprising povidone.

The dosage forms of the present form may be in solid, semi-solid or liquid form. In a preferred aspect, the present invention provides a compressed tablet composition including an ibuprofen medicament, a domperidone medicament and a carrier material comprising a compressed mixture of
(a) a granular component comprising said ibuprofen medicament and at least a first portion of said carrier material; and
(b) a powder component comprising a lubricant material and an optional further portion of said carrier material, said domperidone medicament being present in either of components (a) and (b), characterised in that the carrier material is substantially free of povidone and comprises at least one diluent combined with at least one disintegrating agent.

In a further preferred aspect, the present invention provides a directly compressed tablet composition comprising
(i) an ibuprofen medicament;
(ii) a domperidone medicament; and
(iii) a carrier material characterised in that the carrier material is substantially free of povidone and comprises at least one diluent combined with at least one disintegrating agent and a lubricating agent.

In a further preferred aspect, the present invention provides a solid composition comprising a non-compressed mixture of
(i) an ibuprofen medicament;
(ii) domperidone medicament; and
(iii) a carrier material characterised in that the carrier material is substantially free of povidone and comprises at least one diluent combined with at least one release modifying agent.

In a further preferred aspect, the present invention provides a liquid or semi-solid composition comprising
(i) an ibuprofen medicament;
(ii) a domperidone medicament; and
(iii) a carrier material characterised in that the carrier material is substantially free of povidone and comprises at least one diluent combined with at least one release modifying agent.

In a still further preferred aspect, the present invention provides a solid pharmaceutical composition comprising:
(a) an ibuprofen medicament;
(b) a domperidone medicament; and
(b) a carrier comprising a diluent combined with a disintegrating agent;

characterised in that the carrier is substantially free of water-soluble polyvinylpyrrolidone.

Where WO 98/34612 constitutes prior art, there may be excluded
(a) compositions wherein the carrier comprises a mixture of 15–38% by weight maize starch or 9–11% microcrystalline cellulose in combination with a starch component comprising 3–6% by weight dried maize starch or 6–10% by weight pre-gelled starch;
(b) tablets formed by direct compression containing 9–11% microcrystalline cellulose and 5–6% by weight lactose.

In a still further preferred aspect, the present invention provides a solid pharmaceutical composition formed by compressing a granular composition comprising:
(a) an ibuprofen medicament;
(b) a domperidone medicament; and
(c) a carrier comprising at least one diluent and at least one disintegrating agent said carrier being adapted to combine the ingredients in a stable composition;

optionally combined with other ingredients characterised in that the granular composition is formed by a granulation process in the absence of water-soluble polyvinylpyrrolidone.

The ibuprofen molecule exists in two enantiomeric forms and the term ibuprofen medicament as used herein is intended to embrace the individual enantiomers, especially S(+)-ibuprofen, and mixtures thereof in any proportion including a 1:1 mixture which is herein referred to as racemic ibuprofen. The ibuprofen medicament may be also present in the form of any salt or other derivative of ibuprofen or its enantiomers. If necessary, the ibuprofen medicament may comprise one or more ibuprofen active ingredients such as racemic ibuprofen and S(+)-ibuprofen in combination. However, we prefer that the ibuprofen medicament comprises a single ibuprofen active ingredient. Representative examples of salts of racemic or S(+)-ibuprofen include alkali metal salts, for example the sodium or potassium salts of ibuprofen; alkaline earth metal salts, eg the calcium or magnesium salts of ibuprofen; metal salts, eg the aluminium salt of ibuprofen; amino acid salts for example the lysine or arginine salts of ibuprofen; or amine salts, eg the meglumine salt of ibuprofen. Preferably the ibuprofen medicament is racemic ibuprofen, S(+)-ibuprofen or the sodium or lysine salt thereof, most preferably, racemic ibuprofen.

It is generally desired to have as high a proportion of ibuprofen medicament in the dosage form as possible to reduce the size of the solid dosage form. Representative dosage forms generally comprise ibuprofen medicament to an extent to give 35–90% by weight ibuprofen medicament by weight of the formulation, preferably 35–75% by weight, more preferably 40–70% by weight and most preferably 50–65% by weight. Unit dosages may comprise ibuprofen medicament to an extent of 50 mg, 100 mg, 150 mg, 200 mg, 250 mg, 300 mg, 350 mg, 400 mg, 500 mg, 600 mg and 800 mg. Where salts or other derivatives are employed, usually the precise unit doses are chosen to give the equivalent ibuprofen doses set out above, for example 256 mg of the sodium salt dihydrate or 342 mg of the dl lysine salt provides an equivalent dose to 200 mg ibuprofen. Suitably the pharmaceutical compositions are administered in divided doses throughout the day so the amount of ibuprofen (or the corresponding amount of a salt thereof to be administered at each dosing time is in the range 50 to 800 mg (preferably 50 to 400 mg, more preferably 200 to 400 mg). Therefore, if two dosage forms are to be administered at each time, the dosage forms should contain 25 to 400 mg (preferably 50 to 300 mg, more preferably 100 to 200 mg) ibuprofen medicament.

The domperidone medicament may be in the form of domperidone or a pharmaceutically acceptable salt thereof, particularly acid addition salts such as the maleate. Preferably, the domperidone medicament is in the form of domperidone or the maleate salt.

Representative compositions according to the present invention may comprise the domperidone medicament in an amount 0.1–20% by weight, suitably 0.5–15%, preferably 1–10% and more preferably 1–5% by weight of the composition. Unit dosages may comprise the domperidone medicament to an extent of 5 mg, 10 mg, 15 mg, 20 mg, 25 mg, 30 mg, 40 mg and 50 mg. Suitably the pharmaceutical compositions are administered in divided doses throughout the day so the amount of domperidone (or the corresponding amount of a salt thereof) to be administered at each dosing time is 5 to 50 mg (preferably 5 to 25 mg, more preferably 5 to 20 mg). Therefore, if two dosage forms are to be administered at each time, the dosage forms should contain 2.5 to 25 mg, (preferably 2.5 to 12.5 mg, more preferably 2.5 to 10 mg) domperidone medicament.

Preferred compositions according to the present invention are in the form of a unit dose comprising 50–400 mg ibuprofen medicament and 5–20 mg domperidone medicament. More preferred compositions comprise 100–400 mg or 100–200 mg ibuprofen medicament and 5–10 mg domperidone medicament.

The solid dosage form may be in the form of a controlled release tablet, a suppository, effervescent granules, a chewable tablet and a dissolving buccal dosage form or any other appropriate form. Preferably, the ibuprofen and domperidone medicaments are administered as a compressed solid dosage form, further preferably orally.

Preferred solid dosage forms are in the form of orally administered tablets (conventional, sustained and mixed release profiles), gelatin capsules (hard and soft), dispersible tablets, chewable tablets, effervescent powders and granules. More preferably the solid dosage form is a tablet, either formed by direct compression of the powdered ingredients or by granulating the ibuprofen medicament, in which case the domperidone medicament may be in the granular component or in a powdery component combined with the granular component.

A unit dosage form preferably contains one or two dosage forms, preferably tablets.

The compositions according to the present invention may be adapted for substantially immediate release, for controlled release or there may be a different rate of release for each active ingredient. Thus, the composition may exhibit a range of release profiles. For example the period over which each drug is released may commence shortly after ingestion or, if the dosage form permits, a controlled release may commence after a time. The desired release profile is generally determined by a number of factors, including the nature of the active ingredient, the type of therapy and the nature of the excipient providing controlled release. The composition may optionally be provided with one or more layers which substantially prevent release until the dosage form reaches a certain point in the gastro-intestinal tract (eg determined by pH) or which acts as a barrier and thus reduces the rate of release. There may also be provided optional layers which may also contribute to the release profile of the active ingredients.

The carrier suitably forms up to 65% by weight of the dosage form. Preferred dosage forms include 20–60% by weight carrier, more preferably 25–60% by weight and most preferably 30–50%. The carrier is adapted to combine the components to form a stable solid composition. The ibuprofen and domperidone may thus be combined as a single unit dose, preferably as an intimate admixture together with the carrier.

The carrier consists of non-povidone containing ingredients. The carrier material comprises at least one inert diluent material, for example one or more of sugar diluents, salts and oxides of alkaline earth metals, cellulose diluents, methacrylate diluents starch diluents, glyceryl and vegetable oil diluents. Examples of inert diluent materials include one or more of a sugar material, including sugar alcohols, (eg dextrose, lactose, sucrose, compressible sugar, mannitol and sorbitol), dextrates, dextrin, maltodextrin, calcium carbonate, calcium sulphate, dicalcium phosphate, tricalcium phosphate, glyceryl palmitostearate, hydrogenated vegetable oil (type I), kaolin, magnesium carbonate, magnesium oxide, microcrystalline cellulose, polymethacrylates, potassium chloride, powdered cellulose, hydroxypropylmethyl cellulose, pregelatinised starch, sodium chloride, starches (eg wheat starch, maize starch, potato starch, rice starch, tapioca starch) and modified starches. Preferred diluents have good cohesive properties and serve to bind the materials together. Further preferred diluents are compressible and include a cellulose component, a phosphate component, a starch component or a sugar component or mixtures thereof. Preferred examples of such diluents are microcrystalline cellulose, hydroxypropylmethyl cellulose, dicalcium phosphate, tricalcium phosphate, maltodextrin and soluble sugars such as lactose, sucrose and dextrin, especially microcrystalline cellulose, tricalcium phosphate and lactose. In an especially preferred composition, the carrier material consists essentially of one or more of the following diluents: microcrystalline cellulose, tricalcium phosphate and lactose. The most preferred diluents have a combination of good cohesion (or binding) and good compressibility. These properties may be provided by more than one excipient. These ingredients will be used in the composition in an amount as used by the person skilled in the art This will generally be in the range 10–50% by weight of the composition, preferably 20–50% of the composition, more preferably 20–45% and most preferably 20–35% by weight of the composition.

Some inert diluents also have disintegrating properties, for example microcrystalline cellulose and/or hydroxypropylmethyl cellulose and therefore a discrete disintegrant material is not always necessary as the diluent material is thus combined with a disintegrating agent. However, in conventional or fast release tablets, we prefer to use a discrete disintegrating component in addition to the diluent, whether or not the diluent has disintegrating properties. Other diluents are substantially without disintegrating properties, eg some soluble diluents. This is within the knowledge of a person skilled in the art. Reference may also be made to the Handbook of Pharmaceutical Excipients ($2^{nd}$ Edition, Ed. Wade & Weller).

Examples of disintegrating agents include one or more of alginic acid, calcium carboxymethylcellulose, sodium carboxymethylcellulose, colloidal silicon dioxide, croscarmellose sodium, guar gum, magnesium aluminium silicate, methylcellulose, microcrystalline cellulose, powdered cellulose, starch (eg wheat starch, maize starch, potato starch, rice starch, tapioca starch), pregelatinised starch, sodium alginate, sodium starch glycolate, low-substituted hydroxypropyl cellulose or mixtures thereof. Preferably the composition according to the present invention includes at least one disintegrating agent. Preferred disintegrants comprise one or more of croscarmellose sodium and sodium starch glycolate. These ingredients will be used in the composition in an amount as used by the person skilled in the art. This will generally be in the range up to 15% by weight of the composition, for example 1–10% by weight, preferably 2–8% by weight of the dosage form.

The release modifying agent may also comprise agents which slow down the release of either medicament such as water-swellable polymers (eg cellulose ethers or gums such as xanthan gum and sodium alginate) or film forming polymers (eg ethyl cellulose or acrylic resin).

Preferred compositions comprise 20–60% by weight of carrier material including up to 15% by weight of discrete disintegrant material. Further preferred compositions comprise a carrier material consisting essentially of a diluent substantially without disintegrating properties (for example tricalcium phosphate), a diluent with disintegrating properties (for example microcrystalline cellulose), a discrete disintegrant (for example croscarmellose sodium) and a lubricating agent (for example magnesium stearate or stearic acid).

The composition may also include further ingredients. These ingredients will be used in the composition in an amount as used by the person skilled in the art. These may include a flow aid, such as talc or colloidal silicon dioxide which may preferably be used up to an extent of 4% by weight of the composition, for example 0.5–2.0% by weight of the composition. Lubricants such as stearic acid, sodium lauryl sulphate, polyethylene glycol, hydrogenated vegetable oil, hydrogenated cotton seed oil, calcium stearate, sodium stearyl fumarate or magnesium stearate or mixtures thereof may also be included in the composition. These may be used to an extent of up to 4% by weight of the dosage form, for example 0.5–2% by weight of the composition. Anti-adherents such as talc may further be included in an amount of up to 4% by weight of the composition. For example, 0.5–2% by weight of the composition.

Most commonly, the components will be compressed into tablets in a solid composition according to the present invention. Thus, the carrier is capable of being compressed with the active ingredients to form a robust tablet with cohesive properties. The tabletting process may contain a granulation stage in which at least one of the active ingredients and at least a portion of the diluent is mixed with a granulating fluid, either in the presence or absence of a granulating agent and formed into a granular composition which has sufficient free-flowing and cohesive properties to be capable of further processing with other excipients and compressed into a tablet. The granulation stage may also be carried out under dry conditions, ie in the absence of a granulating fluid.

Thus, in a preferred aspect of the present invention, there is provided a solid pharmaceutical composition comprising a compressed mixture of
(i) granules comprising the ibuprofen medicament and optionally the domperidone medicament, a carrier material including a release-modifying excipient; and
(ii) a lubricant and optionally a flow aid.

The composition may be formed by compressing the granular composition with the lubricant and optional flow aid together with other optional ingredients and is characterised in that the granular composition is formed by a granulation process in the absence of water-soluble polyvinyl pyrrolidone.

The granulation step may be carried out under dry conditions using techniques such as slugging or roller-compaction or by melt-extrusion. It is preferred to include a liquid in the granulation process. This is termed a "wet-granulation" process. In a preferred wet-granulation process, a granulating fluid is used in which the ibuprofen is soluble. Thus, the dissolved ibuprofen, on drying, contributes to the cohesiveness of the granular composition without requiring a granulating agent, such as water-soluble polyvinyl pyrrolidone to be employed in the granulation process. If desired, however, a granulating agent may be employed. A preferred granulating liquid is isopropyl alcohol. In another preferred process a granulating fluid is selected in which the ibuprofen may be substantially insoluble or only partially soluble (eg in water) and it may be of advantage to further include a granulating agent.

In a further preferred aspect of the invention, there is provided a solid pharmaceutical composition comprising as ingredients:—

(a) an ibuprofen medicament;
(b) a domperidone medicament;
(c) a carrier comprising a mixture of an inert diluent, a disintegrating component, at least one diluent having disintegrating properties and a granulating agent said carrier being adapted to combine the ingredients in a stable composition.

Thus, preferably the composition further comprises a granulating agent. The term "granulating agent" and "binding agent" herein are used interchangeably. A wet granulation process is particularly preferred, where the granulating agent imparts cohesive properties to the powdered materials. This may be achieved in the presence of a suitable solvent (preferably water) which causes the granulating agent to stick to the surrounding granular or powdery material and which on drying maintains the cohesion between the particles. Preferably the solid compositions according to the present invention are produced by a process including a wet granulation stage in the presence of a granulating fluid and a granulating agent. The granulating agent may be a solid; it may be present as a solid powder material or it may be dissolved in the granulating fluid. The granulating agent is preferably selected from a polymeric material, eg a natural or synthetic gum, or a cellulose material, a sugar granulating agent and a starch granulating agent. Examples of granulating agents or binders include, as polymeric materials, acacia, alginic acid, carbomer, carboxymethylcellulose sodium, alkyl celluloses (such as methylcellulose and ethylcellulose), gelatin, guar gum, hydroxyalkyl celluloses (such as hydroxyethylcellulose, hydroxypropyl cellulose, hydroxypropylmethyl cellulose), polymethyacrylates, sodium alginate; as sugar granulating agents (including sugar alcohols), liquid glucose, maltodextrin, sucrose and sorbitol; as starch granulating agents, dextrin, pregelatinised starch, starch (eg wheat starch, maize starch, potato starch, rice starch, tapioca starch) and modified starch; and also magnesium aluminium silicate and zein; or mixtures thereof. Preferred polymer materials are hydroxypropyl cellulose and hydroxypropylmethyl cellulose. These ingredients will be used in the composition in an amount as used by the person skilled in the art. This will generally be in the range of up to 10% by weight (eg 0.1–10%), or preferably 0.5–5% by weight and most preferably 2–4%.

In a particularly preferred aspect of the present invention the pharmaceutical composition is in the form of a granulation, ie it is in granular form. In a further preferred aspect, the pharmaceutical composition is a solid dosage form, preferably a tablet.

A composition according to the present invention may be coated, eg with a sugar or film coating which has minimal effect on the disintegration time. A preferred solid dosage form of the present invention, ie a tablet, may be film or sugar coated by conventional coating techniques.

The compositions according to the present invention are formed by combining the ingredients, for example incorporating said ibuprofen medicament and said domperidone medicament with the carrier material as a homogeneous blend, and providing them in a suitable unit dosage form, eg by compression, by a spraying process or by filling into capsules. Preferred dosage forms are prepared by compression eg tablets (including tablets for oral administration, effervescent tablets and tablets adapted to be dispersed in a liquid prior to ingestion), suppositories or inserts and buccal or sub-lingual tablets. In the compression process the tablets are generally formed by a wet granulation, a dry granulation or a direct compression process. In these processes the ingredients are combined as desired, either to form a homogeneous blend which is then compressed into a tablet or to make different blends which are then compressed to make different layers in a tablet. In the wet granulation process, one or both of the active ingredients is homogeneously blended with at least a portion of the carrier and formed into granules by the addition of a granulating fluid preferably in the presence of a granulating agent. Preferably both the ibuprofen medicament and the domperidone medicament are included in the granular product. The granulating agent may be added to (preferably dissolved in) the granulating fluid prior to addition to the blend of active ingredient and carrier or the granulating agent may be blended with the active ingredient and carrier prior to the addition of the granulating fluid. The granulating fluid may be water or an organic solvent, eg a $C_{1-6}$ alkanol such as ethanol, propan-1-ol or propan-2-ol or a mixture thereof. The granulated material is then dried, sieved, added to other ingredients as necessary and blended to form a homogeneous mixture prior to compression into tablets. In the dry granulation process, the ingredients are formed into granules in the absence of a liquid, such as by roller compaction or slugging. The granules are then mixed with the remaining ingredients and compressed into a solid dosage form. The compositions according to the present invention may also be formed by sieving powdered ingredients into a container and then blending to form a homogeneous mixture. The mixture may be directly compressed into tablets. The "direct compression" process does not include a pre-granulation step. The ingredients are combined to form a homogeneous mixture and then fed to a tabletting for compression into tablets.

In a preferred process, the composition is formed by a process including a wet granulation stage as described above. Desirably, both the active ingredients are present in the granular product together with an inert diluent and a disintegrating agent. In a composition prepared by a more preferred process, a granulating agent or binder is present and comprises a cellulose material (more preferably hydroxypropylmethylcellulose). Preferably, the granulating fluid is water. In a further preferred process, the granulating agent or binder is admixed with the powdered excipients and the granulating fluid (preferably water) added thereto. Preferably the granular product is combined with a lubricant and compressed into tablets.

Thus, in a further aspect, the present invention provides a process to prepare a compressed composition comprising (a) granulating said ibuprofen medicament, optionally with said domperidone medicament, with at least a first portion of said carrier material and a granulating fluid; (b) drying said granules; (c) blending with a lubricating agent and optionally a flow aid to form a homogeneous mixture, and (d) compressing into tablets. In such a process, a cellulose material is the preferred granulating agent.

The dosage forms of the present invention may, if desired, include other compatible pharmacologically active ingredients, eg codeine, caffeine or vitamin products.

The ibuprofen/domperidone combination drug treatment is primarily intended for the treatment of migraine and other diseases for which the properties of ibuprofen (especially anti-inflammatory, analgesic and anti-pyretic properties) in combination with the properties of domperidone (especially to treat nausea and dyspepsia) are useful.

In accordance with the present invention there is also provided the use of a carrier material which is substantially free of povidone and which comprises at least one diluent combined with at least one release modifying agent in a stable pharmaceutical composition comprising an ibuprofen medicament and a domperidone medicament. Preferably the release modifying agent is a disintegrating agent.

Further general information concerning the excipients may be obtained from The Handbook of Pharmaceutical Excipients (2nd Edition: Ed Wade and Weller) and Remington: Science and Practice of Pharmacy (19th Ed: Ed Gennaro).

The invention will now be illustrated by the following Examples which are given by way of example only. In these examples the ingredients are obtained from the sources listed below:—

Both microcrystalline cellulose and colloidal cellulose are available under the trade names Avicel and are available from FMC Corporation; Croscarmellose sodium is available from FMC Corporation under the trade name Ac-Di-Sol; Hydrogenated cotton seed oil is available from Edward Mendell under the trade name Lubritab; Hydroxypropyl methylcellulose is available from the Dow Corporation under the trade name Methocel E 50; Hydroxypropyl cellulose is available from the Dow Corporation under the trade name Klucel LF; Colloidal silicon dioxide is available from Degussa under the tradename Aerosil; Xanthan gum is available from Monsanto under the trade name Keltrol; Polysorbate 80 is a polyoxyethylene 20 oleate; Polysorbate 60 is polyoxyethylene 20 stearate.

EXAMPLES 1 to 3

| Ingredient | Example 1 | Example 2 | Example 3 |
|---|---|---|---|
| Ibuprofen | 60.5% | 60.5% | 60.3% |
| Domperidone Maleate | 1.9% | 1.9% | 1.9% |
| Microcrystalline cellulose | 6.1% | 6.1% | — |
| Croscarmellose sodium | 9.7% | 9.7% | 3.0% |
| Magnesium stearate | 0.6% | — | 0.6% |
| Hydrogenated cotton seed oil | — | 0.6% | — |
| Tricalcium phosphate | 18.2% | 18.2% | — |
| Hydroxypropyl cellulose | 3.0% | — | — |
| Hydroxypropylmethyl cellulose | — | 3.0% | — |
| Sorbitol | — | — | 34.2% |

The composition of Example 1 was prepared according to the following steps:—

(a) the ibuprofen, domperidone maleate, tricalcium phosphate, hydroxypropyl cellulose, croscarmellose sodium and microcrystalline cellulose were sieved and blended to form a homogeneous mixture;

(b) the mixture was granulated to a suitable end point with water and dried;

(c) the dried granules were blended with magnesium stearate;

(d) the lubricated granules were compressed to form tablet cores each containing 200 mg of ibuprofen and 5 mg of domperidone or each containing 400 mg of ibuprofen and 10 mg of domperidone;

(e) the tablet cores were coated with a conventional film coating.

Example 2 was prepared in a similar manner as described in Example 1 except that hydroxypropylmethyl cellulose replaced hydroxypropyl cellulose in stage (a) as the granulating agent and hydrogenated cotton seed oil replaced magnesium stearate in stage (c) as the lubricating agent.

Example 3 was prepared in a similar manner as described in Example 1 except that sorbitol replaced the microcrystalline cellulose and tricalcium phosphate and no granulating agent was present in stage (a).

EXAMPLES 4 to 6

| Ingredient | Example 4 | Example 5 | Example 6 |
|---|---|---|---|
| Ibuprofen | 60.5% | 62.4% | 60.5% |
| Domperidone maleate | 1.9% | 2.0% | 1.9% |
| Microcrystalline cellulose | 6.1% | 6.3% | 6.1% |
| Croscarmellose sodium | 9.7% | 10.0% | 9.7% |
| Stearic acid | 0.6% | 0.6% | — |
| Magnesium stearate | — | — | 0.6% |
| Tricalcium phosphate | 18.2% | 18.7% | 18.2% |
| Hydroxypropylmethyl cellulose | 3.0% | — | 3.0% |

The tablet cores contained 200 mg or 400 mg ibuprofen.

Example 4 was prepared in a similar manner as described in Example 1 except that hydroxypropylmethyl cellulose replaced hydroxypropyl cellulose in stage (a) as the granulating agent and stearic acid replaced magnesium stearate as lubricant in stage (c).

Example 5 was prepared in a similar manner as described in Example 1 except that no granulating agent was present in stage (a), isopropanol was used as the granulating fluid in stage (b) and stearic acid replaced magnesium stearate as lubricant in stage (c).

Example 6 was prepared in a similar manner as described in Example 1 except that hydroxypropylmethyl cellulose replaced hydroxypropyl cellulose in stage (a) as granulating agent.

EXAMPLE 7

| Ingredient | % w/w |
|---|---|
| Ibuprofen | 59.8% |
| Domperidone | 1.9% |
| Colloidal silicon dioxide | 0.2% |
| Magnesium stearate | 0.6% |
| Lactose | 9.2% |
| Microcrystalline cellulose | 22.2% |
| Sodium lauryl sulphate | 1.9% |
| Sodium starch glycolate | 3.5% |

The composition of Example 7 was prepared by sieving and blending all the above powdered ingredients to form a homogeneous mixture and compressing to form tablet cores containing 200 mg of ibuprofen and 5 mg equivalent of domperidone or each containing 400 mg of ibuprofen and 10 mg equivalent of domperidone.

There may also be prepared tablets comprising 200 mg ibuprofen and 10 mg equivalent of domperidone or 400 mg ibuprofen and 20 mg equivalent of domperidone prepared as described in any one of Examples 1–7. The racemic ibuprofen in the above Examples may be replaced by a therapeutically equivalent weight of S(+)-ibuprofen or the sodium or lysine salts of racemic ibuprofen or S(+)-ibuprofen.

EXAMPLES 8–35

The following compositions (Examples 8–35) were formed and tested as described below to determine their stability. The ingredients for each Example are set out in Tables 1, 2 and 3.

Examples 8–31 were formed by combining the powder ingredients to form a homogeneous powder blend.

Examples 32–35 were formed by combining the powder ingredients to form a homogenous powder blend and then compressed into tablets.

The Examples were analysed for degradation of the domperidone after storage of the Example compositions for one week under controlled conditions at 50–60° C. for detectable levels of the impurity cis-5-chloro-1-[1-[3-(2,3-dihydro-2-oxo-1H-benzimidazol-1-yl)propyl]piperidin-4-yl]-2,3-dihydro-1H-benzimidazol-2-one-1-oxide (referred to herein as Domperidone N-oxide). This was measured by HPLC analysis. Examples for which no detectable amount of Domperidone-N-oxide was found (<0.1%) were considered satisfactory.

TABLE 1

| | Amount of ingredient (mg) Example | | | | | | | | | |
|---|---|---|---|---|---|---|---|---|---|---|
| | 8 | 9 | 10 | 11 | 12 | 13 | 14 | 15 | 16 | 17 |
| Ibuprofen | 200.0 | 200.0 | 200.0 | 200.0 | 200.0 | 200.0 | 200.0 | 200.0 | 200.0 | 200.0 |
| Domperidone | 2.5 | 2.5 | 2.5 | 2.5 | 2.5 | 2.5 | 2.5 | 2.5 | 2.5 | 2.5 |
| Microcrystalline cellulose | 100.0 | 100.0 | 100.0 | 100.0 | 100.0 | 100.0 | 100.0 | 100.0 | 100.0 | 100.0 |
| Hydroxypropyl methyl cellulose | — | 10.0 | — | — | — | — | 10.0 | — | — | — |
| Sodium lauryl sulphate | — | — | 10.0 | — | — | — | | | | |
| Talc | — | — | — | 10.0 | — | — | | | | |
| Magnesium stearate | — | — | — | — | 10.0 | — | | | | |
| Stearic acid | — | — | — | — | — | 10.0 | | | | |
| Sodium starch glycolate | | | | | | | | — | 10.0 | — | — |
| Hydroxypropyl cellulose | | | | | | | | — | — | 10.0 | — |
| Hydrogenated vegetable oil | | | | | | | | — | — | — | 10.0 |

TABLE 2

| | Amount of ingredient (mg) Example | | | | | | | | | | | | | |
|---|---|---|---|---|---|---|---|---|---|---|---|---|---|---|
| | 18 | 19 | 20 | 21 | 22 | 23 | 24 | 15 | 26 | 27 | 28 | 29 | 30 | 31 |
| Ibuprofen | 200.0 | 200.0 | 200.0 | 200.0 | 200.0 | 200.0 | 200.0 | 200.0 | 200.0 | 200.0 | 200.0 | 200.0 | 200.0 | 200.0 |
| Domperidone | 2.5 | 2.5 | 2.5 | 2.5 | 2.5 | 2.5 | 2.5 | 2.5 | 2.5 | 2.5 | 2.5 | 2.5 | 2.5 | 2.5 |
| Lactose | 100.0 | 100.0 | 100.0 | 100.0 | 100.0 | 100.0 | | | | | | | | |
| Hydroxypropyl methyl cellulose | — | 10.0 | — | — | — | — | | | | | | | | |
| Sodium lauryl sulphate | — | — | 10.0 | — | — | — | | | | | | | | |
| Talc | — | — | — | 10.0 | — | — | | | | | | | | |
| Magnesium stearate | — | — | — | — | 10.0 | — | | | | | | | | |
| Stearic acid | — | — | — | — | — | 10.0 | | | | | | | | |
| Colloidal silicon dioxide | | | | | | | 100.0 | — | — | — | — | — | — | — |
| Tricalcium phosphate | | | | | | | — | 100.0 | — | — | — | — | — | — |
| Maize starch | | | | | | | — | — | 100.0 | — | — | — | — | — |
| Pulverised sugar | | | | | | | — | — | — | 100.0 | — | — | — | — |
| Sorbitol | | | | | | | — | — | — | — | 100.0 | — | — | — |

TABLE 2-continued

| | Amount of ingredient (mg) Example | | | | | | | | | | | | | |
|---|---|---|---|---|---|---|---|---|---|---|---|---|---|---|
| | 18 | 19 | 20 | 21 | 22 | 23 | 24 | 15 | 26 | 27 | 28 | 29 | 30 | 31 |
| Calcium carboxymethyl-cellulose | | | | | | | — | — | — | — | — | 100.0 | — | — |
| Dicalcium phosphate | | | | | | | — | — | — | — | — | — | 100.0 | — |
| Maltodextrin | | | | | | | — | — | — | — | — | — | — | 100.0 |

TABLE 3

| | Amount of ingredient (mg) | | | |
|---|---|---|---|---|
| Example | 32 | 33 | 34 | 35 |
| Ibuprofen | 200.0 | 200.0 | 200.0 | 200.0 |
| Domperidone | 2.5 | 2.5 | 2.5 | 2.5 |
| Microcrystalline cellulose | 100.0 | 100.0 | — | — |
| Lactose | — | — | 100.0 | 100.0 |
| Magnesium stearate | 10.0 | — | 10.0 | — |
| Stearic acid | — | 10.0 | — | 10.0 |

The analysis of Examples 8–35 found no detectable level of Domperidone N-oxide as an impurity (ie <0.1% by weight).

To the ingredients of Examples 8–31 there may be added a disintegrant (eg croscarmellose sodium), a flow aid (eg colloidal silicon dioxide) and also a lubricant (eg magnesium stearate) (as described herein) followed by compression into tablets.

EXAMPLE 36

| Ingredient | % w/w |
|---|---|
| Ibuprofen | 59.9 (200 mg) |
| Domperidone | 0.6 |
| Microcrystalline cellulose | 18.0 |
| Lactose | 12.0 |
| Magnesium stearate | 0.5 |
| Starch | 9.0 |

A tablet formulation containing the ingredients listed above was prepared in a similar manner to that described in Example 3 or by direct compression in a similar manner to that described in Example 7.

The following Example formulations may also be prepared:

EXAMPLE 37

Sustained Release Tablet

| Ingredient | % w/w |
|---|---|
| Domperidone maleate | 3.7 |
| Ibuprofen | 74.1 |
| Xanthan gum | 18.5 |
| Hydroxypropyl methylcellulose | 2.2 |
| Stearic acid | 1.1 |
| Colloidal silicon dioxide | 0.4 |

A sustained release tablet may be prepared by granulating the hydroxypropyl methylcellulose and ibuprofen with approximately 20% of the total content of xanthan gum using water as the granulating agent. The ibuprofen granule is combined with the remainder of the xanthan gum and the other ingredients and compressed into tablets containing 400 mg ibuprofen and 20 mg domperidone.

EXAMPLE 38

Capsule

| Ingredient | % w/w |
|---|---|
| Ibuprofen | 60.6 |
| Domperidone | 3.0 |
| Lactose | 30.3 |
| Croscarmellose sodium | 6.1 |

The ingredients were formed into a homogeneous blend and filled into a conventional hard gelatin capsule containing 200 mg ibuprofen and 10 mg domperidone.

EXAMPLE 39

Liquid Suspension

| Ingredient | % w/w |
|---|---|
| Domperidone maleate | 0.2 |
| Ibuprofen | 2.0 |
| Colloidal cellulose | 2.5 |
| Glycerin | 15.0 |
| Sorbitol | 10.0 |
| Kaolin | 1.0 |
| Polysorbate 80 | 0.1 |
| Purified water BP | to 100 |

The polysorbate 80 may be added to the water followed by the addition of glycerin with stirring. The domperidone and ibuprofen may then be added and also the colloidal cellulose, sorbitol and kaolin (as thickeners) with continued stirring until a satisfactory suspension is formed.

EXAMPLE 40

Effervescent Granules

| Ingredient | % w/w |
| --- | --- |
| Domperidone maleate | 0.3 |
| Ibuprofen | 10.2 |
| Microcrystalline cellulose | 2.5 |
| Pulverised sugar | 51.2 |
| Malic acid | 25.5 |
| Sodium bicarbonate | 7.7 |
| Anhydrous sodium carbonate | 2.6 |
| Sodium lauryl sulphate | 0.1 |

The domperidone, ibuprofen, microcrystalline cellulose and sugar are granulated with water and then thoroughly dried. The remaining ingredients are added to form a powder mixture and filled into sachets each containing 400 mg ibuprofen and 20 mg domperidone maleate.

EXAMPLE 41

Chewable Tablet

| Ingredient | % w/w |
| --- | --- |
| Ibuprofen | 17.6 |
| Domperidone maleate | 0.6 |
| Sucrose | 66.0 |
| Sorbitol | 13.2 |
| Fumed silica | 0.8 |
| Stearic acid | 1.8 |

The above ingredients are combined to form a homogeneous blend followed by direct compression to form a chewable tablet containing 200 mg ibuprofen and 7.5 mg domperidone maleate.

EXAMPLE 42

Suppository

| Ingredient | % w/w |
| --- | --- |
| Domperidone maleate | 0.9 |
| Ibuprofen | 23.6 |
| Polysorbate 60 | 4.7 |
| Witepsol H185 | 70.8 |

The polysorbate is dispersed in the molten Witepsol followed by the addition of the ibuprofen and domperidone. The mixture is then injected into moulds to produce a suppository shape and cooled to ambient temperature. The suppository contains 600 mg ibuprofen and 22.5 mg domperidone maleate.

COMPARATIVE EXAMPLE 1

Ibuprofen (200 mg) and domperidone maleate (2.5 mg) were formed into a granule by a standard granulating process using water and isopropyl alcohol as the granulating fluid. After storage for one week at 50–60° C. no detectable level of Domperidone-N-oxide as impurity (as described in the test described above) was found (ie <0.1%). When povidone (10 mg) was additionally incorporated into the granule an impurity level of greater than 1.5% (as defined above) was found after storage for one week at 50–60° C.

COMPARATIVE EXAMPLE 2

Ibuprofen was combined with domperidone maleate on a conventional mixer to produce a homogenous powder blend containing 200 mg ibuprofen and 2.5 mg domperidone maleate. The product was stored for one week at 50–60° C. On analysing the product after storage, no detectable level of impurity (as defined above) was found to be present.

In contrast, when povidone (20 mg) was incorporated into the powder blend, the level of impurity after storage for one week at 50–60° C. was found to be about of 0.7% by weight. When crospovidone (Kollidon CL) was incorporated into the tablet in replacement for the povidone, the level of impurity (as defined above) after storage for one week at 50–60° C. was found to be about 7.9% by weight.

COMPARATIVE EXAMPLES 3 AND 4

In a similar way to that described in Example 2, povidone (10 mg) was incorporated into the powder blend of Example 8 (comparative Example 3) and also in the powder blend of Example 19 (comparative Example 4), after storage for one week at 50–60° C., the level of impurity (as defined above) was found to be approximately 0.5% by weight. The results with and without povidone (pvp) are given in Table 4 below.

TABLE 4

| Comparative Example | % Impurity (1 week) without pvp | % Impurity (1 week) with pvp |
| --- | --- | --- |
| 3 | <0.1% | ~0.5% |
| 4 | <0.1% | ~0.5% |

What is claimed is:
1. A stable pharmaceutical composition comprising a mixture of
   (i) an ibuprofen medicament;
   (ii) 0.1 to 20% by weight of a domperidone medicament based on the total weight of the composition; and
   (iii) a carrier material
characterized in that the carrier material is substantially free of povidone and comprises at least one diluent combined with at least one disintegrating agent excluding
   (a) a compressed tablet comprising granulated ibuprofen and a carrier-material consisting essentially of either maize starch at 35–38% total tablet weight in combination with dried maize starch at 3–4% total tablet weight or microcrystalline cellulose at 10–11% total tablet weight in combination with croscarmellose sodium at 14–16% total tablet weight and pre-gelled starch at 10% total tablet weight;
   (b) a direct compression tablet comprising a carrier material consisting essentially of microcrystalline cellulose at 8–11% total tablet weight and lactose at 5–6% total tablet weight;

(c) a hard gelatin capsule comprising a carrier consisting essentially of maize starch at 15–20% total capsule contents weight in combination with pre-gelled starch at 5–6% total capsule contents weight.

2. A composition according to claim 1 characterised by further comprising a granulating agent present to an extent of up to 10% of total tablet weight.

3. A composition according to claim 1 further comprising a granulating agent consisting essentially of one or more of the following:
polymeric granulating agents selected from natural gums, synthetic gums and cellulose materials; a sugar granulating agent; a starch granulating agent.

4. A composition according to claim 3 characterised in that the granulating agent is a cellulose derivative.

5. A composition as claimed in claim 1 in the form of a directly compressed tablet composition comprising:
(i) an ibuprofen medicament;
(ii) a domperidone medicament; and
(iii) a carrier material,
characterised in that the carrier material is substantially free of povidone and comprises at least one diluent combined with at least one disintegrating agent and further comprising a lubricating agent.

6. A composition according to claim 1 comprising 20–60% by weight carrier material.

7. A composition according to claim 1 wherein the diluents are selected from microcrystalline cellulose, tricalcium phosphate or lactose.

8. A composition according to claim 1 further comprising one or more discrete disintegrants.

9. A composition according to claim 1 in which the ibuprofen medicament is racemic ibuprofen or S(+)-ibuprofen or the sodium or lysine salts thereof, present to an extent of 50–65% by weight of the composition and the domperidone medicament is domperidone or the maleate salt thereof, present to an extent of 1–5% of the composition.

10. A process to prepare a composition according to claim 1 comprising (a) granulating said ibuprofen medicament, with said domperidone medicament, with at least a first portion of said carrier material and a granulating fluid; (b) drying said granules; (c) blending with a lubricating agent and optionally a flow aid to form a homogeneous mixture, and (d) compressing into tablets.

11. A process according to claim 10 further comprising a cellulose material as a granulating agent.

12. A method of treating migraine which comprises the administration to a patient in need thereof a stable pharmaceutical composition according to claim 1.

13. A composition according to claim 4 characterised in that the cellulose derivative is hydroxypropyl cellulose or hydroxypropyl methylcellulose.

14. A composition according to claim 6, further comprising up to 15% by weight of a discrete disintegrant material.

15. A composition according to claim 8 wherein the discrete disintegrant is selected from the group consisting of comprising croscarmellose sodium and sodium starch glycolate.

* * * * *